United States Patent [19]

Rapp

[11] Patent Number: 5,156,841

[45] Date of Patent: Oct. 20, 1992

[54] ANTI-TUMOR VACCINE

[75] Inventor: Ulf R. Rapp, Washington, D.C.

[73] Assignee: United States of America, Washington, D.C.

[21] Appl. No.: 236,947

[22] Filed: Aug. 26, 1988

[51] Int. Cl.$^5$ .................... A61K 39/00; A61K 37/02
[52] U.S. Cl. ......................................... 424/88; 514/21
[58] Field of Search ....................... 514/2, 21; 530/300, 530/350, 358, 403, 806; 424/88

[56] References Cited

U.S. PATENT DOCUMENTS 4,701,442 10/1987 Revici .................................. 514/21
4,720,386 1/1988 McCollester ......................... 424/88

OTHER PUBLICATIONS

Chang et al., Relationship Between T-Antigen and Tumor-Specific Transplantation Antigen in Simian Virus 40-Transformed Cells, Journal of Virology, vol. 29, No. 1, pp. 69–74, 1979.

Hanahan, Heritable Formation of Pancreatic B-Cell Tumours in Transgenic Mice Expressing Recombinant Insulin/Simian Virus 40 Oncogenes Nature, vol. 315, pp. 115–122, issue of May 9, 1985.

Watt et al., "Expression and Characterization of the Human C-Myc DNA-Biding Protein", Mol. Cell. Biol. 5: 448–456 (1985).

Tevethia et al., "Biology of Simian Virus 40 (SU40) Transplantation Antigen (TrAg)", Virol. 107: 13–23 (1980).

George E. Mark and Ulf R. Rapp, "Primary Structure of V-Raf: Relatedness to the SRC Family of Oncogenes", Science (1984) 224:285–289.

P. Sutrave et al., "Nucleotide Sequence of Avian Retroviral Oncogene V-Mil: Homologue of Murine Retroviral Oncogene V-Raf", Nature (1984) 309:85–88.

Primary Examiner—John Doll
Assistant Examiner—George C. Elliott
Attorney, Agent, or Firm—Cushman, Darby & Cushman

[57] ABSTRACT

An antitumor vaccine utilizing oncoproteins as immunogen is disclosed. The oncoprotein could be administered either as isolated, substantially pure product or expressed through a recombinant vaccinia virus containing either the complete coding sequence for the oncoprotein(s) or portions thereof.

3 Claims, 2 Drawing Sheets

ANTI-TUMOR VACCINE

TECHNICAL FIELD

The present invention relates generally to cancer therapy. More particularly, the present invention relates to an anti-tumor vaccine utilizing oncoproteins as immunogen, either alone or in combination with other oncoproteins or potentiating agents.

BACKGROUND OF THE INVENTION

Oncogenes are one of the several cancer or tumor causing factors. Oncogenes direct the synthesis of oncoproteins which differ from their normal counterparts in either structure and/or quantity per cell. Through certain mechanisms, which are not yet fully understood, oncoproteins may convert the normal cells into cancerous entities.

Immunotherapy utilizing monoclonal antibodies directed against tumor marker antigens, which are normal cell products, has been attempted as a modality in the treatment of cancer. However, this procedure has certain limitations or disadvantages:

(a) It introduces foreign protein (monoclonal antibodies) into the patient;
(b) Tumor-specific structure of antigens is usually undetermined; and
(c) Functional significance of the antigen for the cell is often unknown.

In contrast, oncoproteins are known to be responsible for the continual growth of the tumor cells. Furthermore, oncoproteins are often immunogenic in their natural host and their presence on tumor cells renders the antigen presenting cells susceptible to immune surveillance. Despite such knowledge, however, the efficacy and potency of oncoproteins as immunogenic agents for the treatment of cancer have not yet been fully determined.

SUMMARY OF THE INVENTION

It is, therefore, an object of the present invention to provide a vaccine employing oncoproteins as immunogen.

It is a further object of the present invention to provide a method of treating host derived cancer by inducing anti-oncoprotein antibodies in a host susceptible to or suffering from cancer.

It is another object of the present invention to provide a method of inhibiting carcinogen induced cancer.

It is an additional object of the present invention to provide an animal model for testing anti-tumor agents, vaccines and the like.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 (A) and (B) shows the mortality curves of NFS×AKR F1 mice treated with ENU+BHT ( ○ ) and those treated with ENU+BHT and vaccinated weekly with purified oncoprotein ( ◇ ). FIG. 1 (A) shows ENU versus ENU+BHT, where     means 2A-ENU+Oil and     means 2B,6B-ENU+BHT.

FIG. 1(B) shows ENU+BHT versus ENU+RAF+BHT, where     means 2B,6B-ENU+BHT and     means ENU+RAF+BUT.

DETAILED DESCRIPTION OF THE INVENTION

Figure 1A:
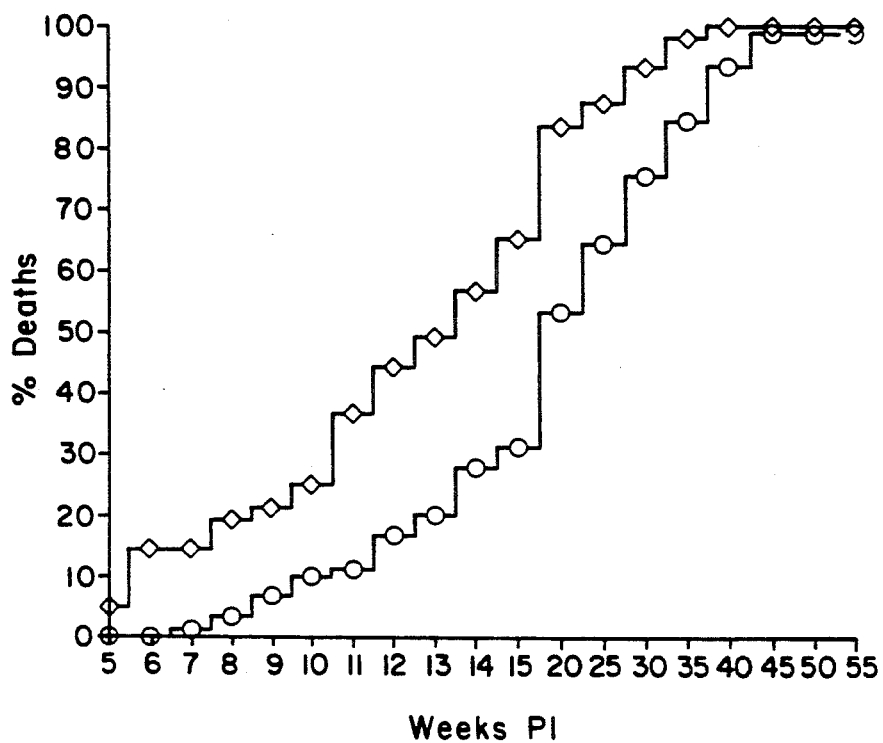

The above and various other objects and advantages of the present invention are achieved by a vaccine, comprising an immunogenic amount of isolated, substantially pure oncoprotein either alone or in combination with other oncoprotein(s) or potentiating factors. A method of treating cancer comprises inducing sufficient amount of anti-oncoprotein immune response to neutralize cancer causing oncoprotein in a host susceptible to or suffering from cancer. Of course, the oncoprotein can be utilized either in whole or in part and in combination with a plurality of other oncoproteins. An animal mode as described herein can be used to test the anti-cancer agents.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art. The term "substantially pure" as used herein means a product which is as pure as can be obtained by employing standard purification methodology well known to one of ordinary skill in the art.

The term "other potentiating factor or agent" as used herein means other oncoproteins or parts thereof and a general immune system stimulant such as Freund's adjuvant and the like.

In order to test the efficacy of the anti-tumor vaccine of the present invention, first a model system was developed. The system comprises an animal model for generating lung carcinoma which is the most prevalent cancer in the Western world. NFS mice are mated with AKR males and the pregnant mice are transplacentally injected at day 16 of gestation with ethylnitrosourea (ENU) at a dosage of 0.5 mmole/kg body weight of the mother. Then tumor promotion in weanling F1 is begun with weekly injections of butylated hydroxytoluene (BHT, 2 mg/10 g body weight). The offspring rapidly develop tumors starting at about 5 weeks of age. Two types of tumors result: lung adenocarcinoma (80%-100%) and T-cell lymphomas (60%-70%). It was found that the expression of c-raf-1 RNA and protein was very high in both types of tumor cells relative to the control tissue. Furthermore, live cell fluorescence indicated surface expression of the predominantly cytoplasmic raf protein in tumor cells (data not shown). It was for this reason that raf oncoprotein was selected to determine whether induction of an immune response to raf oncoprotein in these mice would affect tumor development.

Accordingly, raf oncoprotein was produced in *Escherichia coli* with the aid of an expression plasmid following standard techniques well known in the art. The oncoprotein was then isolated from refractile bodies and purified by standard procedures such as high pressure liquid chromatography employing routine methodology. The isolated, substantially pure raf oncoprotein thus obtained was then used to vaccinate the carcinogen, tumor bearing F1 mice on a weekly regimen. The raf protein was injected into the animals intraperitoneally in Freund's adjuvant at a dose of 3 micrograms per week.

Figure 1B:
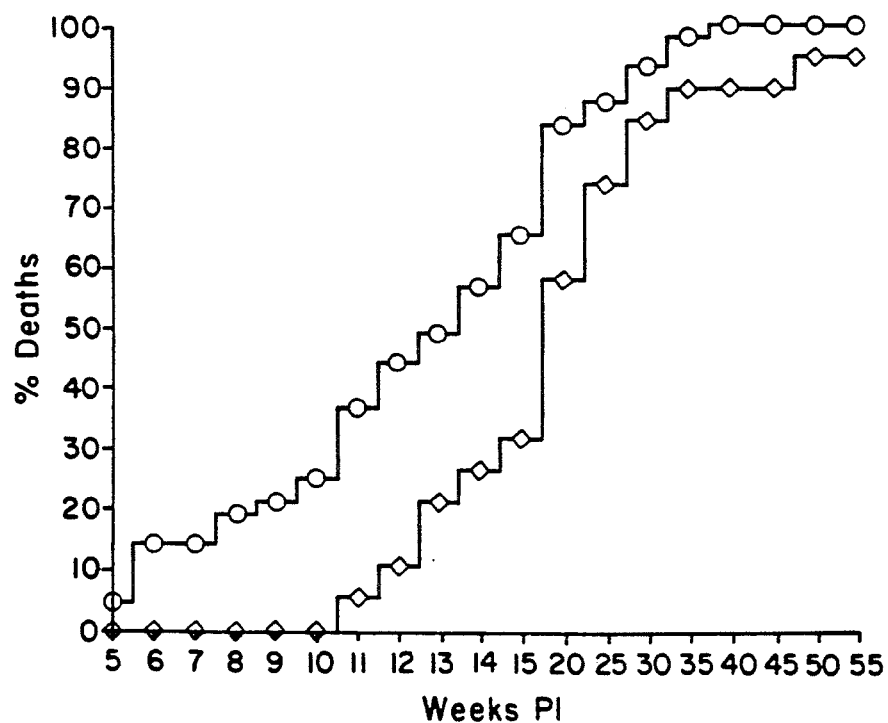

FIG. 1 shows the mortality curves of NFS×AKR F1 mice treated with ENU+BHT (○) and of those treated with ENU+BHT and vaccinated weekly with purified raf protein (◇). The results clearly demonstrate the marked protective effect on tumor latency and development in the vaccinated mice. Both the initial and the mean time for tumorigenesis doubled with vaccinations at 2, 3 and 4 weeks of age. Statistical analysis demonstrated the significance of the achieved attenuation at a confidence limited of greater than 99.5% for a 2-tailed Cox test.

To further establish the efficacy of raf vaccination on tumor initiation and development, another strategy was followed. A eukaryotic expression vector, vaccinia virus, was employed as a vehicle for constitutive expression of the oncoprotein as opposed to the externally introduced, purified oncoprotein which may remain present and intact in the animal only for a relatively short period of time and may even become partially denatured or degraded during isolation. Since a second raf family oncogene A-raf occurs in an activated form in the carcinogen induced T-cell lymphomas generated in the tumor induction model described herein, A-raf was included in the vaccinia virus constructions. In addition to the preparation of the raf containing vaccinia recombinant, a myc containing vaccinia recombinant was also constructed (FIG. 2B). The reasoning behind myc carrying viruses is that since myc is a nuclear oncogene while raf is primarily cytoplasmic, a combination of such nuclear and cytoplasmic oncogenes may produce a synergistic effect in lung tumor development. Moreover, myc family genes are commonly found to be over expressed in lung tumors. Thus a vaccination with both oncoproteins, either sequentially or simultaneously may provide a more efficient and effective treatment regimen.

Figure 2A:
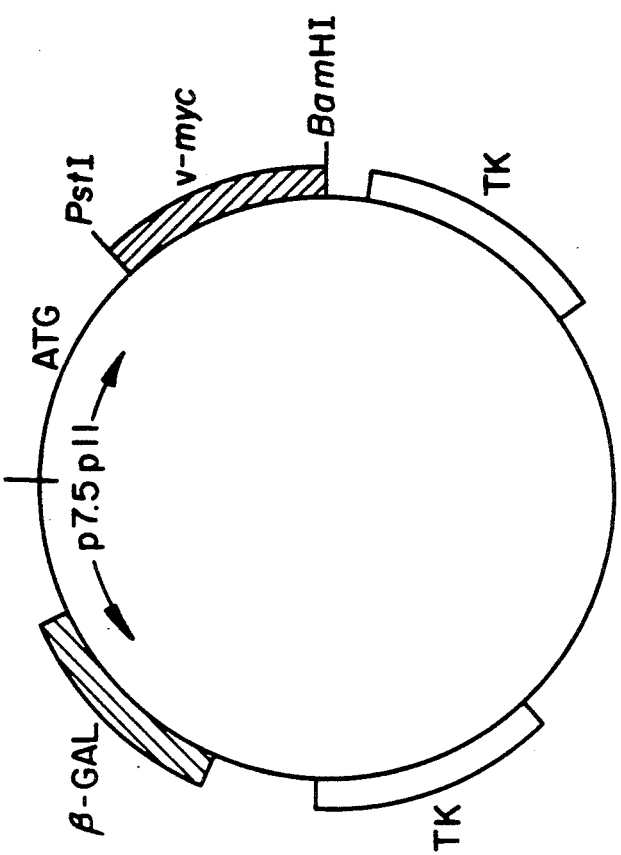
FIG. 2 (A) and (B) show the schematic construction of raf (A) and myc (B) carrying plasmids used for in vivo virus recombinations.
Figure 2B:
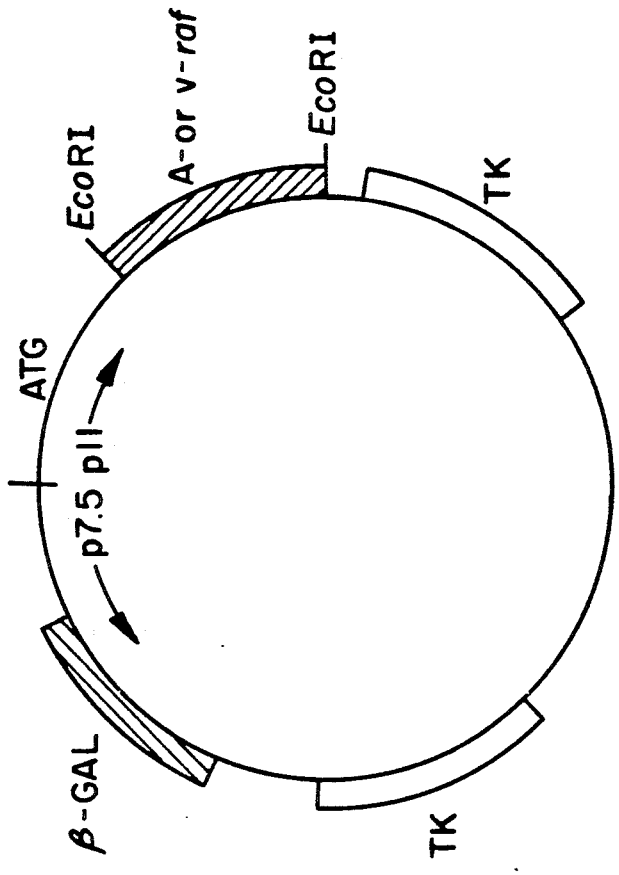

The construction of raf and myc vaccinia recombination plasmids for use in vivo is shown schematically in FIGS. 2(A) and (B).

Vaccinia Virus Vaccination

NFS females are mated with AKR males. Animals are paired in different groups, one control and three experimental. For group 1, the control group, no treatment is given to either the parents or offspring. The other three groups each receive the following treatment. On day 16 of gestation (counting plug dates as day 1) pregnant females are given a transplacental injection of ethylnitrosourea (ENU) (dissolved in citrate buffer), at a concentration of about 0.1 ml of a 50 mM solution per 10 g body weight. Offsprings then receive weekly injections of butylated hydroxytoluene (BHT) (dissolved in corn oil) at a concentration of 0.1 ml of a 20 mg/ml solution per 10 g body weight, beginning at five weeks of age. Group 2 then receives no further treatment. Group three litters are exposed to a raf expressing vaccinia virus at three weeks of age. Group four litters are exposed to a myc expressing vaccinia virus at three weeks of age. Exposure to virus is via a tail-rub, wherein the tail is rubbed with a slightly abrasive material and virus spotted onto the area. Approximately 10 litters per group are used. Inoculation with recombinant vaccinia virus can be similarly utilized in other hosts. The results clearly indicate the efficacy of the treatment described herein.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A vaccine, comprising an effective amount of a host-cell associated intracellular raf oncoprotein in a pharmacologically acceptable vehicle, to delay the onset and development of tumorigenesis associated with said raf oncoprotein in said host, when said host is vaccinated with said raf oncoprotein.

2. The vaccine of claim 1 wherein said oncoprotein is c-raf-1.

3. A method for inducing protection against a cancer associated with an oncoprotein, comprising vaccinating a host susceptible to said cancer with an effective amount of the vaccine of claim 1.

* * * * *